United States Patent
Spinella et al.

(10) Patent No.: US 10,876,713 B2
(45) Date of Patent: Dec. 29, 2020

(54) LIGHT ASSEMBLY AND METHOD FOR OPERATING THEREOF

(71) Applicant: STMicroelectronics S.r.l., Agrate Brianza (IT)

(72) Inventors: Giuseppe Spinella, Biancavilla (IT); Enrico Rosario Alessi, Catania (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

(21) Appl. No.: 16/819,744

(22) Filed: Mar. 16, 2020

(65) Prior Publication Data

US 2020/0318812 A1  Oct. 8, 2020

(30) Foreign Application Priority Data

Apr. 5, 2019   (IT) .......................... 10 2019 0005242

(51) Int. Cl.
*F21V 15/00*   (2015.01)
*F21V 5/00*   (2018.01)
(Continued)

(52) U.S. Cl.
CPC ................ *F21V 15/00* (2013.01); *F21V 5/00* (2013.01); *F21V 14/00* (2013.01); *G01N 21/255* (2013.01);
(Continued)

(58) Field of Classification Search
CPC . F21V 15/00; F21V 5/00; F21V 14/00; F21Y 2115/10; G01N 21/255;
(Continued)

(56) References Cited

U.S. PATENT DOCUMENTS 9,435,527 B1 *  9/2016  Kluska ................ H05K 1/0272
2011/0051423 A1   3/2011  Hand et al.
(Continued)

FOREIGN PATENT DOCUMENTS

WO   2014106121 A1   7/2014

OTHER PUBLICATIONS

Jenkins, Devon, et al., "LED Performance and Application Considerations for Industrial Environments", 2017 Annual Pulp, Paper and Forest Industries Technical Conference (PPFIC), Jun. 18-23, 2017, 7 pages.

*Primary Examiner* — Zheng Song
(74) *Attorney, Agent, or Firm* — Slater Matsil, LLP

(57) ABSTRACT

In one embodiment, a light assembly includes a base substrate; a light-emitting device supported by the base substrate; a cover permeable to volatile compounds, completely surrounding the light-emitting device and being transparent to a light flux emitted, during use, by the light-emitting device; a gas sensor configured to sense the volatile compounds, the gas sensor being arranged within the cover. The light assembly includes a pump having an inlet operatively coupled to the cover, and operable to generate a pressure depression within the cover. The light assembly includes a light sensor operatively coupled to the light-emitting device, the light sensor being configured to sense a light intensity value of at least one light component of the light flux. The light assembly includes a processor operatively coupled to the gas sensor, the light sensor, and the pump; a non-volatile memory storing a program to be executed in the processor.

20 Claims, 2 Drawing Sheets

(51) Int. Cl.

| | |
|---|---|
| *F21V 14/00* | (2018.01) |
| *H01L 31/167* | (2006.01) |
| *H01L 31/02* | (2006.01) |
| *G01N 33/00* | (2006.01) |
| *G01N 21/25* | (2006.01) |
| *H01L 31/0232* | (2014.01) |
| *F21Y 115/10* | (2016.01) |

(52) U.S. Cl.
CPC ... *G01N 33/0047* (2013.01); *H01L 31/02005* (2013.01); *H01L 31/02019* (2013.01); *H01L 31/02327* (2013.01); *H01L 31/167* (2013.01); *F21Y 2115/10* (2016.08); *G01N 2201/062* (2013.01)

(58) Field of Classification Search
CPC .......... G01N 33/0047; G01N 2201/062; H01L 31/02005; H01L 31/02019; H01L 31/02327; H01L 31/167
See application file for complete search history.

(56) References Cited

U.S. PATENT DOCUMENTS

| | | | |
|---|---|---|---|
| 2014/0009295 A1* | 1/2014 | Kim | F21V 33/0076 |
| | | | 340/632 |
| 2015/0382426 A1 | 12/2015 | Odnoblyudov et al. | |
| 2017/0074828 A1* | 3/2017 | Kim | G01N 27/66 |
| 2018/0347797 A1* | 12/2018 | Nicholas | G01J 1/30 |
| 2019/0017659 A1 | 1/2019 | Dendorfer et al. | |
| 2019/0277487 A1* | 9/2019 | Ren | F21K 9/232 |

\* cited by examiner

LIGHT ASSEMBLY AND METHOD FOR OPERATING THEREOF

CROSS-REFERENCE TO RELATED APPLICATIONS

This application claims priority to Italian Patent Application No. 102019000005242, filed on Apr. 5, 2019, which application is hereby incorporated herein by reference.

TECHNICAL FIELD

The present invention relates to lighting, and particularly to light assembly and method for operating thereof.

BACKGROUND

Almost any technology field involving lighting is nowadays demanding an increasing light-flux together with minimum power consumption, specifically for use in energy-saving applications and to increase lighting effectiveness.

Through the use of light emitting diodes (LEDs), manufactures from a variety of fields can easily switch from one color to another using the same light-emitting element, modulate the light-flux intensity, decrease manufacturing costs and save power and space. These advantages are a direct effect of the intrinsic power efficiency, robustness, flexibility and small form factor of the LEDs. It is therefore not surprising that the LED-lighting is rapidly superseding other light-generation ways.

Furthermore, since the LED element is a silicon based product it is well suited for having a smart control, through an integrated circuit, embedded on the same package.

SUMMARY

In one embodiment, a light assembly includes a base substrate; a light-emitting device supported by the base substrate; a cover permeable to volatile compounds, completely surrounding the light-emitting device and being transparent to a light flux emitted, during use, by the light-emitting device; a gas sensor configured to sense the volatile compounds, the gas sensor being arranged within the cover. The light assembly includes a pump having an inlet operatively coupled to the cover, and operable to generate a pressure depression within the cover. The light assembly includes a light sensor operatively coupled to the light-emitting device, the light sensor being configured to sense a light intensity value of at least one light component of the light flux. The light assembly includes a processor operatively coupled to the gas sensor, the light sensor, and the pump; a non-volatile memory storing a program to be executed in the processor. The processor when executing program is configured to: acquire, from the gas sensor, a first signal indicative of a quantity of volatile compounds permeating the cover; acquire, from the light sensor, a second signal correlated to the light intensity value; and activate the pump to generate the pressure depression when both the first and second signals meet a respective predefined condition.

In another embodiment, a light assembly includes a light emitting diode (LED) package including a base substrate, a LED, a gas sensor, a light sensor attached to a first side of the base substrate, a cover permeable to volatile compounds, completely surrounding the LED, the gas sensor, and the light sensor, the cover being transparent to light emitted from the LED, the gas sensor being configured to sense the volatile compounds, the light sensor being configured to sense a light intensity value of at least one light component of the light emitted from the LED. The light assembly includes a circuit board including a pump, where a second side of the base substrate is attached to the circuit board, where the pump is fluidly coupled to the cover through a through hole in the base substrate.

In one embodiment, a method for operating a light assembly includes receiving, at a processor from a gas sensor disposed in the light assembly, a first signal indicative of a quantity of volatile compounds permeating a cover of the light assembly. The method includes receiving, at the processor from a light sensor disposed in the light assembly, a second signal correlated to a light intensity value emitted from a light emitting device disposed in the light assembly. The method includes sending a control signal from the processor to a pump disposed in the light assembly. The method includes activating the pump to generate a pressure depression when both the first and second signals meet a respective predefined condition, where the light sensor, the gas sensor, and the light emitting device are disposed on a base substrate, where the cover surrounds the light sensor, the gas sensor, and the light emitting device, where the pump and the processor are disposed over a circuit board, where pump includes an inlet operatively coupled to the cover and configured to generate the pressure depression within the cover.

BRIEF DESCRIPTION OF THE DRAWINGS

For a better understanding of the present invention, preferred embodiments thereof are now described, purely by way of non-limiting example and with reference to the attached drawings, wherein.

DETAILED DESCRIPTION OF ILLUSTRATIVE EMBODIMENTS

Embodiments of the present invention relates to a light-emitting unit and a method for operating the light-emitting unit. In particular, the light emitting unit includes a light-emitting device, provided with a gas sensor to sense volatile compounds and a light sensor to detect a light-intensity discoloration level of the light flux emitted by the light-emitting device. Embodiments of the present invention further relates to a method of operating the light-emitting unit.

Power LEDs light flux shows a degradation, namely a "discoloration" phenomenon, in presence of volatile organic compounds (VOCs). The presence of chemically-incompatible VOCs on, or near, the LEDs degrades the light output levels and/or cause changes in the chromaticity point of the light.

According to some manufactures' indications, proper design and adequate testing can prevent the discoloration; it is also advised to use only compatible materials (i.e. material free of VOCs) to embed LEDs.

However, in lighting systems based on power LEDs, ventilation apertures are needed in the package housing the LEDs for cooling down the LEDs; these apertures provide a passage for VOCs from the outer environment (among others contaminants) to enter within the package and causing the discoloration phenomenon. The same issue arises if the package sealant is permeable to VOCs (for instance, VOCs can move through the silicone sealant), or if the package sealant is damaged.

On top of that, at the time being, power LEDs are preferred in industrial lighting, automobiles lighting systems, emergency signaling and medium-distance warning systems in which having an effective led driving technique is a key point for having market success introducing smart solutions; in such scenarios, light-flux stability, uniformity of emitted colors, and an excellent power control are of outmost importance.

Various embodiments provide a light-emitting unit and a method for operating the light-emitting unit, to overcome the problems previously illustrated.

Figure 1:
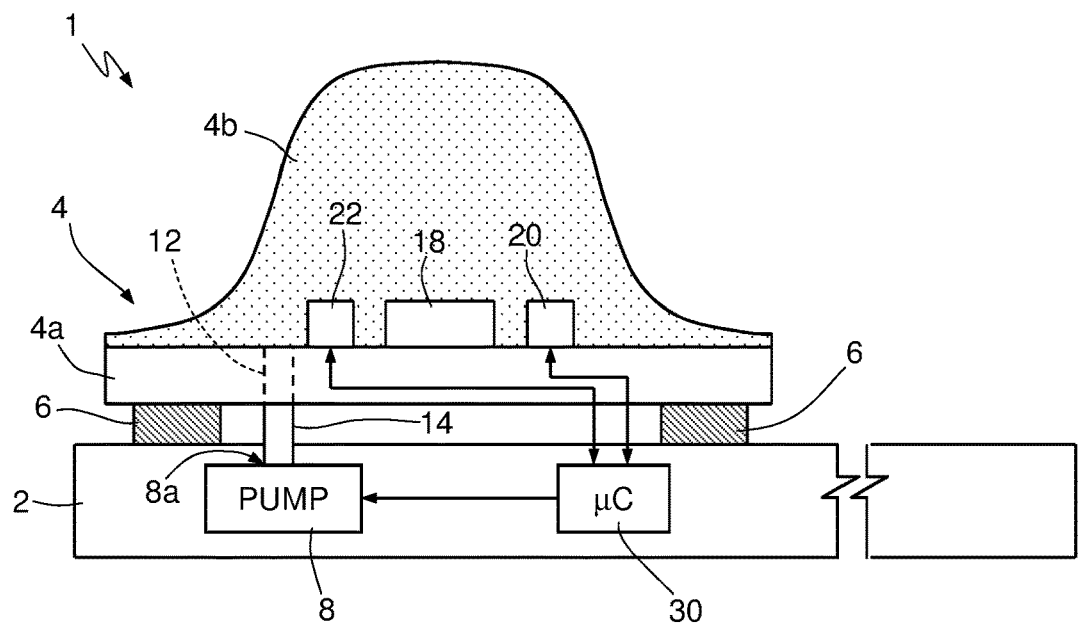
FIG. 1 shows a cross-sectional view of a light assembly according to an embodiment of the present invention.

FIG. 1 illustrates in a tri-axial system of orthogonal axis X, Y, Z, a light-emitting unit 1, in particular a LED unit, according to an embodiment of the present invention.

The LED unit 1 comprises a solid board 2, namely a printed circuit board (PCB); and a LED package 4, electrically and mechanically coupled to the board 2, through coupling regions 6 (e.g., soldering regions).

The LED package 4 includes a substrate 4a, provided with a through hole 12. A covering region 4b extends on the substrate 4a; the covering region 4b (having, in particular, a "dome"-like shape) is, in an embodiment, of silicone material and forms a silicone lens.

The package 4 houses, within the covering region 4b: a light emitting diode (LED) 18 configured to emit a light flux; a gas sensor 20 configured to sense the presence, within the covering region 4b, of one or more type of volatile organic compounds (VOCs); and a light sensor 22 configured to sense at least one component among red, green and blue, of the light flux emitted by the LED 18, and/or configured to sense a light intensity level of the light flux emitted by the LED 18. The LED 18, gas sensor 20 and light sensor 22 are exemplarily coupled to the substrate 4a, in a per se known way.

The covering region 4b is permeable to VOCs, which can accumulate within the covering region 4b and reach the surface of the LED 18, causing the discoloration phenomenon. The VOCs permeating the covering region 4b also reach the sensing element of the gas sensor 20, which provides an output signal indicative of the presence of VOCs within the covering region 4b and on the surface of the LED 18.

The covering region 4b is, in one embodiment, uniform in terms of material density (e.g., it is of silicone); the gas sensor 20, the light sensor 22 and the LED 18 are embedded, or immersed, in the covering region 4b. In other words, the gas sensor 20, the light sensor 22 and the LED 18 are completely surrounded by the covering region 4b, and the covering region 4b is in direct contact with the gas sensor 20, the light sensor 22 and the LED 18.

In another embodiment, the covering region 4b has an inner cavity, and the gas sensor 20, the light sensor 22 and the LED 18 are arranged in said cavity.

In general, the light sensor 22 can be arranged within the covering region 4b, or otherwise placed outside the covering region 4b, and located with respect to the LED device 18/package 4 in such a way to receive the light flux emitted by the LED 18 and sense a light intensity value of at least one component (e.g., at least one among red, green, blue) of the emitted light flux.

The LED 18 is, in one embodiment, a blue LED chip, covered by phosphors. However, the present description relates generally to any type of LEDs, irrespective of the type of light colours emitted.

The board 2 integrates, or houses otherwise, a pump 8 (e.g., a micro pump or a MEMS pump). The pump 8 has an inlet 8a that is coupled, through a tube or conduct or duct 14 passing through the hole 12, to an inner portion of the covering region 4b, so that the pump 8 can be operated to suck air/gases within the covering region 4b, to create a pressure depression within the covering region 4b (in particular, a local depression where the duct 14 is coupled to the covering region 4b). VOCs present (trapped) in the silicone material of the covering region 4b are therefore forced to move (flow) towards the inlet 8a/duct 14, to be removed by the action of the pump 8. VOCs on the surface of the LED 18 are equally forced to move (flow) towards the inlet 8a of the pump 8, to be sucked out. Analogously, also VOCs on the sensing element of the gas sensor 20 are forced to move (flow) towards the inlet 8a of the pump 8, to be sucked out as well.

A processor, or controller, 30 is operatively coupled to the gas sensor 20 and light sensor 22, and to the pump 8. The processor, or controller, 30 can be a microprocessor or microcontroller, integrated in the board 2; however, other technical solutions are practicable, for example the processor, or controller, 30 may be part of a computer (or other computing means) external to the board 2. The processor, or controller, 30 may comprise a non-volatile memory (or be coupled to a non-volatile memory) comprising a program with instructions that is executable by processor, or controller, 30.

The processor 30 can also be coupled to the LED 18, for turning on/off the LED 18 according to the use foreseen for the LED 18. Alternatively, the LED 18 can be turned on and off by a further controller, not shown.

In one embodiment, the gas sensor 20 is a semiconductor-based gas sensor, more in particular a Metal Oxide (MOX) Semiconductor gas sensor. In this case, the measured MOX-resistance (that is the sensing material) is proportional to the VOCs concentration. This level is typically converted in ppm by means of calibration curves computed by the built-in logic of the sensor itself, or alternatively by the processor 30.

In one exemplary and non-limiting embodiment, the gas sensor 20 is configured to operate in a temperature range: −40° C.-+85° C., with a power consumption: down to 1 mW in pulsed mode. The output interfaces are SPI and I2C. The operational gas range is 0.5 ppm-100 ppm TVOC, with a gas sensor response time ≤5 s and a gas accuracy of about 1 ppm. Other types of gas sensors can be used, as apparent to the skilled person in the art.

As light sensor 22 (sensing either the RGB components or the intensity of the light flux), a possible solution includes digital sensor integrating on a same chip a sensing element, an AFE (analog front end), a filter and a digital interface. Other integrated features can be present, such as TOF (Time of Flight) capabilities. Sensors of this type include the ST VL6180X (proximity, gesture and ambient light sensing, ALS, module).

Furthermore, the board 2 may also integrate a Bluetooth low energy wireless network processor, and/or a chip antenna, for managing wireless transfer of data and providing connectivity capabilities, and/or a Bluetooth Low Energy Impedance Matched Balun Filter. Other connectivity protocols can be implemented and used.

Figure 2:
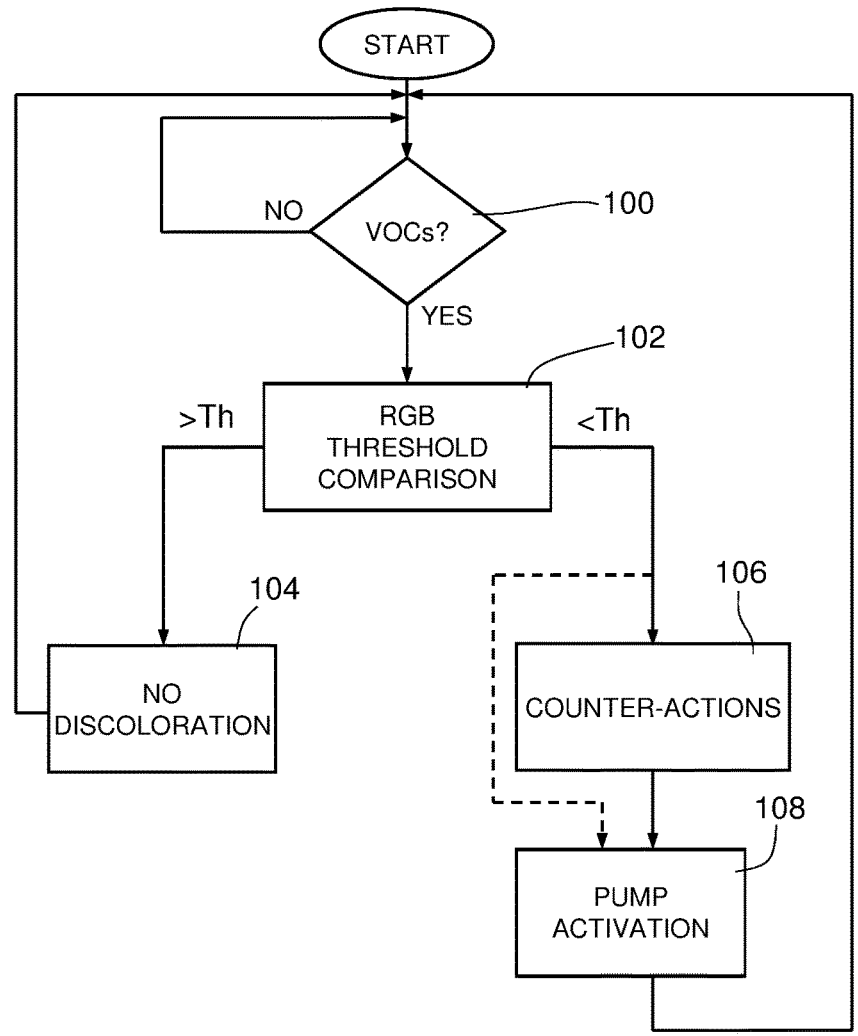
FIG. 2 is a diagram showing a method for operating the light-emitting unit of FIG. 1.

A method of functioning of the LED unit 1 is schematically shown in FIG. 2, and discussed hereunder.

During use, the gas sensor 20 sense (continuously, or at certain predetermined time intervals, or when controlled by the processor 30) the presence of VOCs (FIG. 2, step 100). According to one embodiment, in case no VOCs are detected, or VOCs below a minimum threshold (exit NO from step 100), no further actions are taken and the gas sensor 20 remains in the sensing state. Exit NO from step 100 may include the further step of communicating to the processor 30 a signal indicative of no VOCs, and the processor 30 may use this information as a confirmation of correct functioning of the LED unit 1.

In case the gas sensor 20 senses the presence of VOCs, or an amount of VOCs above a maximum threshold (exit YES from step 100), the processor 30 is informed accordingly (i.e., the gas sensor 20 issues a corresponding signal, indicative of the presence of VOCs, to the processor 30).

The processor 30 then controls the light sensor 22 to acquire information related to the light flux emitted by the LED 18, step 102. In particular, the light sensor 22 acquires one among: the light intensity of the red component only of the light flux; the light intensity of the green component only of the light flux; the light intensity of the blue component only of the light flux. As a further embodiment, the light intensity of two or more components (red, green, blue) of the light flux can be acquired by the light sensor 22. Moreover, as a still further embodiment, the light sensor 22 acquires the light intensity of the light flux without discriminating one or more RGB components. These embodiments may also be combined together.

The light sensor 22 generates an output signal (e.g., one or more light-intensity values) that is indicative of a quality of the light flux emitted by the LED 18, namely it is indicative of a discoloration of the LED 18.

The output signal generated by the light sensor 22 is acquired by the processor 30, which compares the intensity value(s) received with a respective predefined threshold. If the intensity value(s) meet a predefined requisite (e.g., the intensity value concerned is above the threshold), the LED unit 1 is deemed to be in good working condition (no discoloration is present), step 104; otherwise (e.g., the intensity value concerned is below the threshold), the LED unit 1 requires assistance (a discoloration is present) and one or more counter-actions are optionally taken, step 106. During step 106, for example, one or more of the following actions are carried out: (i) the driving power of the LED 18 is increased to maintain the light flux outputted at a desired/expected value (e.g., the value expected in the absence of the discoloration phenomenon); (ii) a warning signal is issued, for remote alert/monitoring.

In case more intensity values are sent by the light sensor 22 to the processor 30, the LED unit 1 requires assistance when at least one intensity value does not meet the predefined requisite (e.g., below threshold). Other embodiments are possible, i.e. assistance is needed when at least two, or all, intensity values do not meet the predefined requisite.

Whether or not step 106 is carried out, when the output of step 102 indicates that the LED unit 1 requires assistance, the processor 30 controls the pump 8 in a working condition, to perform a VOC-cleaning operation, step 108. In particular, the pump 8 is activated by a control signal received from the processor 30 so that a depression is locally generated in correspondence of the duct 14, causing a forced flow of VOCs from the covering region 4b (and from the surface OF LED 18) to the pump 8, VOCs can therefore be actively removed.

By maintaining the pump 8 activated for an opportune period of time, VOCs are effectively removed from the LED 18. The period of time depends on the diffusion dynamics of the gas in a specific material, as understandable to the skilled person in the art.

During the cleaning operation of step 108, the gas sensor 20 can be controlled by the processor 30 to continuously sense the presence of VOCs in the covering region 4b. In this case, the pump 8 is maintained activated by the processor 30 until the gas sensor 20 issues a signal indicative of no VOCs (or VOCs below the minimum threshold) in the covering region 4b.

Step 100, and subsequent steps, are then repeated.

According to a different embodiment, not shown, steps 100 and step 102 can be carried out in inverse order. In this case, the light intensity emitted by the LED 18 is monitored. In case the light intensity sensed differs from the light intensity expected (e.g., it is below a threshold), then the presence of VOCs is sensed through the gas sensor 20. If the output from the gas sensor 20 is interpreted by the processor 30 as a confirmation of the presence of VOCs, then step 108 is performed; otherwise, the decrease in light intensity is ascribed to the ageing of the LED 18 (other procedures may then be followed, not part of the present invention).

Figure 3:
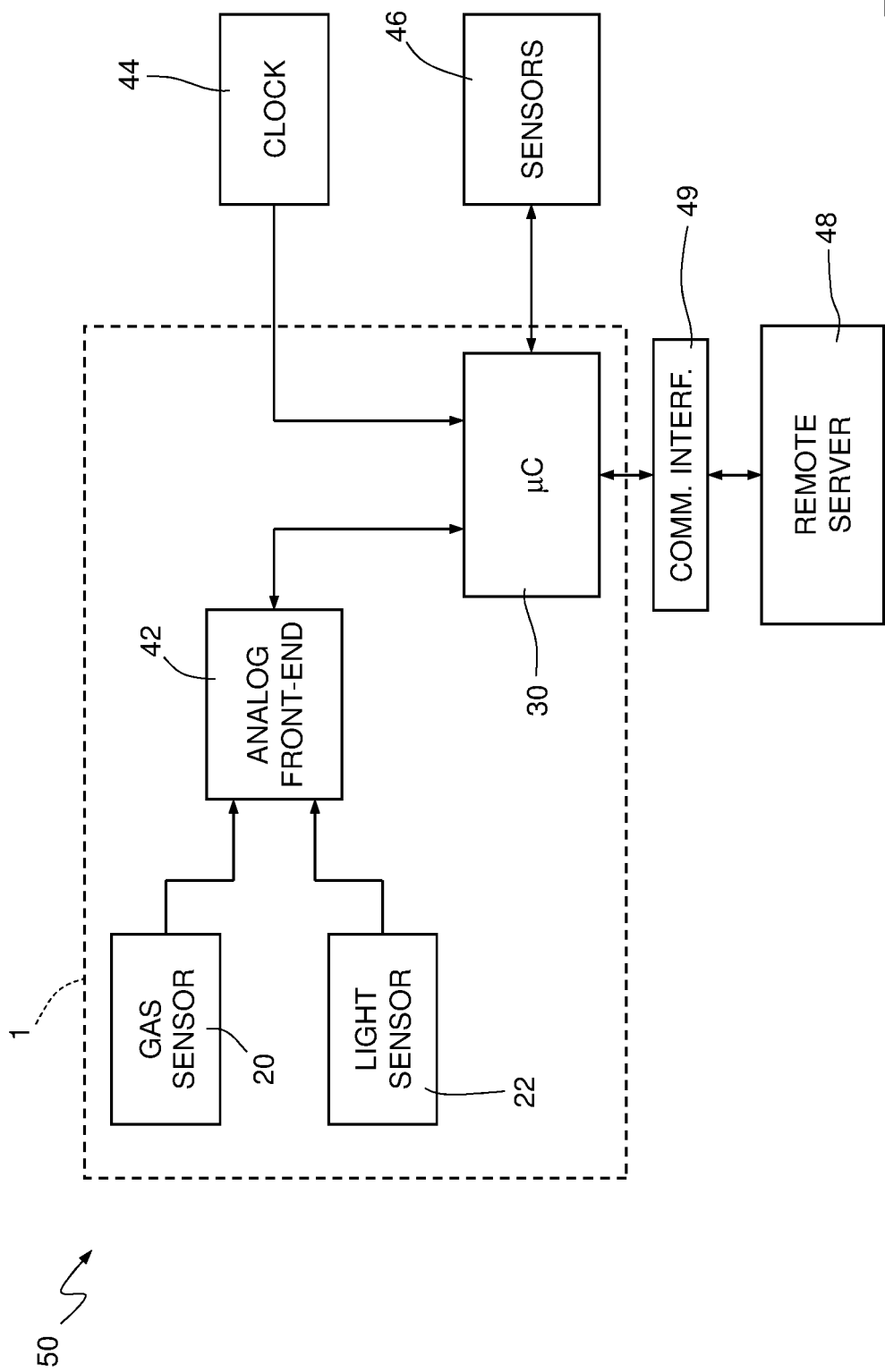
FIG. 3 is a schematic view of a system including the light-emitting unit of FIG. 1.

FIG. 3 schematically shows a system 50, which implements the method of FIG. 2. The system 50 includes the LED unit 1. In addition to the previous description, FIG. 3 shows the presence of an analog front-end 42, which forms an interface between the gas sensor 20 and the processor 30, and between the light sensor 22 and the processor 30, in order to adapt/convert the sensors' output signals to a form which can be accepted as input by the processor 30.

In one embodiment, the analog front-end 42 is integrated in the gas and light sensors 20, 22, together with an analog-to-digital converting circuitry and digital processing features (e.g., for filtering the output). In such a scenario, each of the gas sensor 20 and the light sensor 22 has its own analog front-end 42 providing a digital output to the processor 30.

In another embodiment, the circuitry implementing the analog front-end 42 is external to the gas and light sensors 20, 22 and implements both sensors reading capability and analog-to-digital conversion for the processor 30.

The processor 30 implements a main logic. For example, the main logic is a discrete-time processing logic with a limited number of states and connections in order to keep low the computational complexity and latency. The main logic has a limited number of transitions, as shown in the diagram of FIG. 2, driven by low computational workload based on continuous VOC-gradient and light-gradient computation.

A clock 44, which can be mounted/integrated on the board 2 or be external to the board 2, is coupled to the processor 30 to provide the required timing for implementing the method of FIG. 2. The clock 44 may also be part of the processor 30, in a per se known way.

A further sensor block 46 can optionally be present, and includes MEMS sensors for motion detection (accelerometers, gyroscopes, etc.), temperature sensors, and other detectors, as needed. The sensor block 46 is optional.

A remote server 48, dislocated at a distance from the LED unit 1, is coupled to the processor 30 through a communication interface 49 and a wired or wireless communication channel. The communication interface 49 can be mounted on, or integrated in, the board 2, or be arranged external to the board 2. The remote server 48 receives, for example, the warning signal issued at step 106. An operator of the remote server 48 can also manually trigger the start of the method of FIG. 2.

Embodiments of the present invention are applicable to the fields of industrial lighting, automobiles lighting systems, emergency signaling, medium-distance warning systems and portable electronic devices. Other application fields are possible, as apparent to the skilled person in the art.

The advantages of embodiments of the invention described previously emerge clearly from the foregoing description.

In particular, embodiments of the present invention enable signalling, prevent maintenance, and guarantee constant light flux for the entire life span of the LED device.

The embodiments of the present invention make use of miniaturized and process-compatible, low cost, VOC and light sensors, thus guaranteeing cost saving, low consumption, and high-level of integration.

Finally, it is clear that modifications and variations may be made to what has been described and illustrated herein, without thereby departing from the scope of the present invention, as defined in the annexed claims.

For example, the LED 18 can be instead a LASER, or another light-emitting device subject, during use, to discoloration phenomena caused by volatile compounds (not necessarily of organic type).

Moreover, a further coating may be present above the covering region 4b (lens); such further coating is transparent to the light flux emitted by the light-emitting diode (LED) 18.

Furthermore, it is apparent that the package 4 may house, in the covering region 4b, more than one LED 18 and/or more than one gas sensor 20 (e.g., for redundancy) and/or more than one light sensor 22 (e.g., for redundancy).

According to embodiments of the present invention, a light-emitting unit and a method for operating the light-emitting unit are provided, as defined in the annexed claims.

What is claimed is:

1. A light assembly comprising:
   a base substrate;
   a light-emitting device supported by the base substrate;
   a cover permeable to volatile compounds, completely surrounding the light-emitting device and being transparent to a light flux emitted, during use, by the light-emitting device;
   a gas sensor configured to sense the volatile compounds, the gas sensor being arranged within the cover;
   a pump having an inlet operatively coupled to the cover, and operable to generate a pressure depression within the cover;
   a light sensor operatively coupled to the light-emitting device, the light sensor being configured to sense a light intensity value of at least one light component of the light flux; and
   a processor operatively coupled to the gas sensor, the light sensor, and the pump;
   a non-volatile memory storing a program to be executed in the processor, the processor when executing program is configured to:
      acquire, from the gas sensor, a first signal indicative of a quantity of volatile compounds permeating the cover;
      acquire, from the light sensor, a second signal correlated to the light intensity value; and
      activate the pump to generate the pressure depression when both the first and second signals meet a respective predefined condition.

2. The light assembly according to claim 1, wherein the first signal meets the respective predefined condition when the first signal is indicative of a quantity of volatile compounds above a first threshold, and wherein the second signal meets the respective predefined condition when the second signal is indicative of a light intensity value below a second threshold.

3. The light assembly according to claim 2, wherein, when the pump is activated, the program is configured to cause the processor to:
   acquire, from the gas sensor, continuously or at successive time instants, the first signal to monitor the quantity of the volatile compounds; and
   maintain the pump activated as long as the quantity monitored indicates that volatile compounds are above the first threshold.

4. The light assembly according to claim 1, further comprising:
   a printed circuit board supporting the base substrate,
   wherein the light-emitting device, the gas sensor, and the light sensor are coupled to the base substrate and embedded in the cover, and wherein the pump is mechanically coupled to the printed circuit board and operatively coupled to the cover through a duct extending from the pump inlet to the cover through the base substrate.

5. The light assembly according to claim 1, wherein the cover is a focusing lens for shaping the light flux emitted by the light-emitting device.

6. The light assembly according to claim 1, wherein the cover is of silicone material, the light-emitting device is a light-emitting diode (LED), and the volatile compounds are volatile organic compounds,
   the pump being controllable in activation by the processor with a power adapted to generate a flow of the volatile organic compounds from the LED towards the pump inlet.

7. The light assembly according to claim 6, wherein the volatile organic compounds degrade the light flux when deposited above and in contact with the LED.

8. The light assembly according to claim 1, wherein the first signal is generated by volatile compounds deposited on a sensing element of the gas sensor that is sensitive to the volatile compounds.

9. A light assembly comprising:
   a light emitting diode (LED) package comprising a base substrate, a LED, a gas sensor, a light sensor attached to a first side of the base substrate, a cover permeable to volatile compounds, completely surrounding the LED, the gas sensor, and the light sensor, the cover being transparent to light emitted from the LED, the gas sensor being configured to sense the volatile compounds, the light sensor being configured to sense a light intensity value of at least one light component of the light emitted from the LED; and
   a circuit board comprising a pump, wherein a second side of the base substrate is attached to the circuit board, wherein the pump is fluidly coupled to the cover through a through hole in the base substrate.

10. The light assembly according to claim 9, further comprising:
    a processor operatively coupled to the gas sensor, the light sensor, and the pump;

a non-volatile memory storing a program to be executed in the processor, the processor when executing the program is configured to:
    acquire, from the gas sensor, a first signal indicative of a quantity of volatile compounds permeating the cover;
    acquire, from the light sensor, a second signal correlated to a light intensity value of the light emitted from the LED; and
    activate the pump to generate a pressure depression when both the first and second signals meet a respective predefined condition.

11. The light assembly according to claim 10, wherein the first signal meets the respective predefined condition when the first signal is indicative of a quantity of volatile compounds above a first threshold, and wherein the second signal meets the respective predefined condition when the second signal is indicative of a light intensity value below a second threshold.

12. The light assembly according to claim 11, wherein, when the pump is activated, the program is configured to cause the processor to:
    acquire, from the gas sensor, continuously or at successive time instants, the first signal to monitor the quantity of the volatile compounds; and
    maintain the pump activated as long as the quantity monitored indicates that volatile compounds are above the first threshold.

13. The light assembly according to claim 10, wherein the pump is controllable in activation by the processor with a power adapted to generate a flow of the volatile compounds from the LED towards a pump inlet of the pump.

14. The light assembly according to claim 9, wherein the cover comprises silicone, and the volatile compounds comprise volatile organic compounds.

15. A method for operating a light assembly, the method comprising:
    receiving, at a processor from a gas sensor disposed in the light assembly, a first signal indicative of a quantity of volatile compounds permeating a cover of the light assembly;
    receiving, at the processor from a light sensor disposed in the light assembly, a second signal correlated to a light intensity value emitted from a light emitting device disposed in the light assembly;
    sending a control signal from the processor to a pump disposed in the light assembly; and
    activating the pump to generate a pressure depression when both the first and second signals meet a respective predefined condition, wherein the light sensor, the gas sensor, and the light emitting device are disposed on a base substrate, wherein the cover surrounds the light sensor, the gas sensor, and the light emitting device, wherein the pump and the processor are disposed over a circuit board, wherein pump comprises an inlet operatively coupled to the cover and configured to generate the pressure depression within the cover.

16. The method according to claim 15, wherein the first signal meets the respective predefined condition when the first signal is indicative of a quantity of volatile compounds above a first threshold, and wherein the second signal meets the respective predefined condition when the second signal is indicative of a light intensity value below a second threshold.

17. The method according to claim 16, after the step of activating the pump, the method further comprising:
    acquiring, from the gas sensor, continuously or at successive time instants, the first signal to monitor the quantity of the volatile compounds; and
    maintaining the pump activated as long as the quantity monitored indicates that volatile compounds are above the first threshold.

18. The method according to claim 15, wherein the cover is of silicone material, the light emitting device is a light-emitting diode, and the volatile compounds are volatile organic compounds.

19. The method according to claim 18, wherein the volatile organic compounds when deposited above and in contact with the light-emitting diode degrade the light emitted from the light-emitting diode.

20. The method according to claim 15, further comprising generating a flow of the volatile compounds from the cover towards the pump inlet.

\* \* \* \* \*